(12) United States Patent
Tramontina

(10) Patent No.: US 7,699,189 B2
(45) Date of Patent: Apr. 20, 2010

(54) DISPENSER ASSEMBLY FOR DISPENSING GLOVES INCLUDING GLOVE POSITIONER

(75) Inventor: Paul Francis Tramontina, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 714 days.

(21) Appl. No.: 11/469,542

(22) Filed: Sep. 1, 2006

(65) Prior Publication Data

US 2007/0215628 A1 Sep. 20, 2007

Related U.S. Application Data

(60) Provisional application No. 60/743,572, filed on Mar. 20, 2006.

(51) Int. Cl.
*B65H 3/00* (2006.01)

(52) U.S. Cl. .............................. 221/36; 221/34; 221/35; 221/52; 221/56; 221/58

(58) Field of Classification Search ................. 221/254, 221/36, 56, 58, 34, 35, 52
See application file for complete search history.

(56) References Cited

U.S. PATENT DOCUMENTS

| | | |
|---|---|---|
| 1,959,614 A | 5/1934 | Coons |
| 2,122,637 A | 7/1938 | Colburn |
| 2,591,855 A | 4/1952 | Nicholson |
| 2,795,353 A | 6/1957 | Tuttle |
| 3,174,643 A | 3/1965 | Carlson |
| 3,343,716 A | 9/1967 | Peebles |
| 3,517,855 A | 6/1970 | Hillis |
| 4,623,074 A | 11/1986 | Dearwester |
| 4,773,532 A | 9/1988 | Stephenson |
| 4,844,293 A | 7/1989 | McLaughlin |
| 4,909,413 A | 3/1990 | McCutcheon |
| 4,941,591 A | 7/1990 | Lin et al. |
| 4,953,747 A * | 9/1990 | Wenkman et al. ............. 221/45 |
| 4,993,589 A | 2/1991 | McLaughlin |
| 4,997,105 A * | 3/1991 | Fischer ........................ 221/45 |
| 5,024,349 A | 6/1991 | Haenni et al. |
| 5,096,089 A | 3/1992 | McLaughlin |
| 5,570,808 A | 11/1996 | Tassoni |
| 5,816,440 A | 10/1998 | Shields et al. |

(Continued)

FOREIGN PATENT DOCUMENTS

DE 8715996 U1 2/1988

(Continued)

*Primary Examiner*—Gene Crawford
*Assistant Examiner*—Timothy R Waggoner
(74) *Attorney, Agent, or Firm*—Ralph H. Dean, Jr.

(57) ABSTRACT

A dispensing assembly adapted for dispensing gloves, which includes a dispenser. The dispenser has a housing which forms an inner surface and an internal compartment configured to hold a stack of gloves, and at least one dispensing opening. A stack of gloves disposed in the dispenser on a glove positioner and the glove positioner biases the stack of gloves toward the dispensing opening and a portion of the housing such that the glove positioner controls the stack of gloves and space in the internal compartment of the dispenser to prevent gloves from moving out of the stack and into the space to permit easy and reliable withdrawal of each glove therefrom.

10 Claims, 9 Drawing Sheets

U.S. PATENT DOCUMENTS

| | | | |
|---|---|---|---|
| 5,921,434 A * | 7/1999 | Hollander et al. | 221/34 |
| 5,992,683 A * | 11/1999 | Sigl | 221/59 |
| 5,997,928 A | 12/1999 | Kaish et al. | |
| 6,021,919 A | 2/2000 | Kelly | |
| 6,062,421 A | 5/2000 | Marley | |
| 6,422,416 B1 | 7/2002 | Tramontina | |
| 6,443,327 B1 | 9/2002 | Chen | |
| 6,708,841 B2 | 3/2004 | Baughman | |
| 6,832,697 B2 | 12/2004 | Lai | |
| 2002/0113079 A1 | 8/2002 | Corbett | |
| 2003/0201276 A1 | 10/2003 | Fuller | |
| 2003/0230591 A1 | 12/2003 | Jordan et al. | |
| 2004/0099623 A1 | 5/2004 | Kurtz et al. | |
| 2004/0182874 A1 | 9/2004 | Kringel et al. | |
| 2007/0215630 A1 | 9/2007 | Tramontina | |
| 2007/0215635 A1 | 9/2007 | Tramontina | |

FOREIGN PATENT DOCUMENTS

| | | |
|---|---|---|
| DE | 29818035 | 3/1989 |
| DE | 29616735 | 2/1997 |
| EP | 0305236 | 4/1999 |
| FR | 2776269 | 9/1999 |

* cited by examiner

DISPENSER ASSEMBLY FOR DISPENSING GLOVES INCLUDING GLOVE POSITIONER

CROSS-REFERENCE TO RELATED APPLICATIONS

This application claims priority to U.S. Provisional Application No. 60/743,572, filed Mar. 20, 2006, entitled "Dispenser Assembly For Dispensing Gloves Including Glove Positioner" by Paul Francis Tramontina.

BACKGROUND OF THE INVENTION

This invention relates to a dispenser adapted to hold and dispense a plurality of gloves. Laboratory or industrial glove dispensing systems typically consist of quantities of gloves that are contained in a corrugated box with a perforated region. When the perforated region is removed, an opening is provided through which gloves are withdrawn by a user. Problems exist with this system.

Gloves may be positioned to dispense in a vertical position. When the gloves are presented vertically, one or more portions of gloves often protrude through the opening when the dispenser is nearly or completely filled with a plurality of gloves. When the dispenser is completely or nearly full, it can be difficult for a user to grasp one glove without causing inadvertent dispensing of additional gloves, resulting in waste. Once the first 10 to 20 percent of the gloves are dispensed, problems continue to exist. At this point, a space between the opening and the plurality of gloves is created. This space requires a user to place a portion of his/her hand into the opening to grasp a glove. As this space increases when 30 percent of more of the gloves are dispensed from the dispenser, the gloves have a tendency to collapse from their dispensing position and to clump together at the bottom of the dispenser. This results in a user having to place his/her hand deep into the dispenser to obtain a single glove. Similar problems exist in horizontal dispensing.

In a dispenser which dispenses gloves in a horizontal position, the same problems occur when the dispenser is nearly or completely full of gloves. Again, once the first 10-20 percent of gloves are dispensed, the user is required to place his/her hand into the opening of the dispenser to retrieve a glove. While clumping may not occur, the continued admittance of user hands into a dispenser opening may result in contamination of one or more gloves, or the entire internal compartment of the dispenser and most or all of the plurality of gloves. In addition, in either horizontal or vertical dispensing, the space which occurs between the dispensing opening and the gloves permits contaminants to enter the dispenser.

Accordingly, there is a need for a dispenser assembly which is configured to hold and dispense a plurality of gloves and which maintains gloves continuously next to a dispensing opening. Such a dispenser assembly desirably permits a plurality of gloves to be easily dispensed one at a time. Such a dispenser also desirably permits the gloves to be oriented such that a wrist area or cuff of at least some of the gloves is presented at the opening for a user to grasp for withdrawal. In addition, the opening to the dispenser is desirably configured and positioned such that little surface area of the glove adjacent the opening is exposed. The gloves are desirably positioned in such a dispenser so that only one glove at a time is positioned adjacent an opening. Such a dispenser also is desirably configured to operate and dispense gloves in a horizontal, vertical or oblique position. The dispenser assembly desirably is portable and easily mounted, if desired, on a surface.

DEFINITIONS

As used herein, the term "glove" or "plurality of gloves" refers to a covering for a user's hand, and desirably, but not by way of limitation, includes four fingers and a thumb, an area covering a palm and a back of a user's hand, as well as a cuff positioned generally around a user's wrist. Each glove may be constructed from one or more materials. Such materials may include, for example, but not by way of limitation, a woven material, a nonwoven material, a knitted material, and so forth. In addition, as a further example only, each glove may be constructed from one or more natural or synthetic materials such as latex, nitrile, and so forth, or may be constructed from a combination of materials.

As used herein, the terms "comprise", "comprises", "comprising" and other derivatives from the root term "comprise" are intended to be open-ended terms that specify the presence of any stated features, elements, integers, steps, or components, but do not preclude the presence or addition of one or more other features, elements, integers, steps, components, or groups thereof. Similarly, the terms "include", "includes", "has" and/or "have", and derivatives thereof, are intended to be interpreted as the word "comprise", and are intended to be open-ended terms that specify the presence of any stated features, elements, integers, steps, or components, but do not preclude the presence or addition of one or more other features, elements, integers, steps, components, or groups thereof.

As used herein, the terms "resilient", "resilience" and/or "resiliency" and any derivatives thereof refers to the physical property of an object and/or a material that can return to its original form, shape and/or position after deformation such as being bent, compressed, or stretched that does not exceed its elastic limit.

As used herein, the terms "contaminate", "contaminant" and/or "contamination" mean to make unclean or impure by contact. Such contact may be by liquid, solid and/or gas. For example, but not by way of limitation, mud that befouls shoes; noxious fumes that foul the air; bodily fluids that foul clean diapers.

As used herein, the term "exit port" or "dispensing opening" is the opening in a dispenser for the passage of one or more gloves therethrough.

As used herein, the term "fasteners" means devices that fasten, join, connect, secure, hold, or clamp components together. Fasteners include, but are not limited to, screws, nuts and bolts, rivets, snap-fits, tacks, nails, loop fasteners, and interlocking male/female connectors, such as fishhook connectors, a fish hook connector includes a male portion with a protrusion on its circumference. Inserting the male portion into the female portion substantially permanently locks the two portions together.

As used herein, the term "couple" includes, but is not limited to, joining, connecting, fastening, linking, or associating two things integrally or interstitially together.

As used herein, the term "configure" or "configuration", and derivatives thereof means to design, arrange, set up, or shape with a view to specific applications or uses. For example: a military vehicle that was configured for rough terrain; configured the computer by setting the system's parameters.

As used herein, the term "substantially" refers to something which is done to a great extent or degree; a significant or great amount; for example, as used herein "substantially" as applied to "substantially" covered means that a thing is at least 90% covered.

As used herein, the term "alignment" refers to the spatial property possessed by an arrangement or position of things in a straight line or in parallel lines.

As used herein, the terms "orientation" or "position" used interchangeably herein refer to the spatial property of a place where or way in which something is situated; for example, "the position of the hands on the clock."

As used herein, the term "about" refers to an amount that is plus or minus 10 percent of a stated or implied range.

These terms may be defined with additional language in the remaining portions of the specification.

SUMMARY OF THE INVENTION

In response to the difficulties and problems discussed herein, a dispensing assembly adapted for dispensing gloves is provided. The dispensing assembly includes a dispenser having a housing comprising a plurality of walls which cooperate to form an inner surface and an internal compartment. The housing includes at least one dispensing opening. The housing is configured to hold a stack of gloves and a stack of gloves is disposed therein. The stack of gloves forms a sloping stack positioned against a glove positioner which is positioned in the internal compartment of the housing. The glove positioner and the sloping stack form a trapezoidal cross-section in the internal compartment of the housing. The glove positioner is configured to hold the sloping stack of gloves in an alignment within the internal compartment of the dispenser to prevent gloves from moving out of the stack and into space in the internal compartment and to keep at least one glove positioned against the dispensing opening of the dispenser to permit easy and reliable withdrawal of gloves therefrom.

In another aspect of the invention, a dispensing assembly adapted for dispensing gloves is provided. The dispensing assembly includes a dispenser having a housing comprising a plurality of walls which cooperate to form an inner surface and an internal compartment. The dispenser is configured to hold a stack of gloves and a stack of gloves is disposed in the dispenser. The dispenser includes a dispensing opening. The stack of gloves is positioned on a glove positioner including a resilient material such that the stack of gloves forms a trapezoidal cross-section within the internal compartment of the dispenser. The glove positioner biases the stack of gloves toward the dispensing opening and a portion of the housing. The glove positioner controls the stack of gloves and space in the internal compartment of the dispenser to prevent gloves from moving out of the stack and into the space. The stack of gloves is biased against the dispensing opening to permit easy and reliable withdrawal of each glove therefrom.

In yet another aspect of the invention, a dispensing assembly adapted for dispensing gloves is provided. The dispensing assembly includes a dispenser having a housing comprising a plurality of walls which cooperate to form an inner surface and an internal compartment. The dispenser is configured to hold a stack of gloves and a stack of gloves is disposed in the dispenser. The dispenser includes a pair of spaced-apart dispensing openings. The stack of gloves is positioned on a glove positioner having a pair of opposing ends such that gloves are positioned in a stack cuff-to-cuff at each end of the glove positioner which positions each cuff of a glove adjacent one of the dispensing openings. The glove positioner includes a resilient material which biases the stack of gloves toward the dispensing opening and a portion of the housing such that the glove positioner controls the stack of gloves and space in the internal compartment of the dispenser to prevent gloves from moving out of the stack and into the space. The stack of gloves is biased against the dispensing openings to permit easy and reliable withdrawal of each glove therefrom.

DETAILED DESCRIPTION

Figure 1:
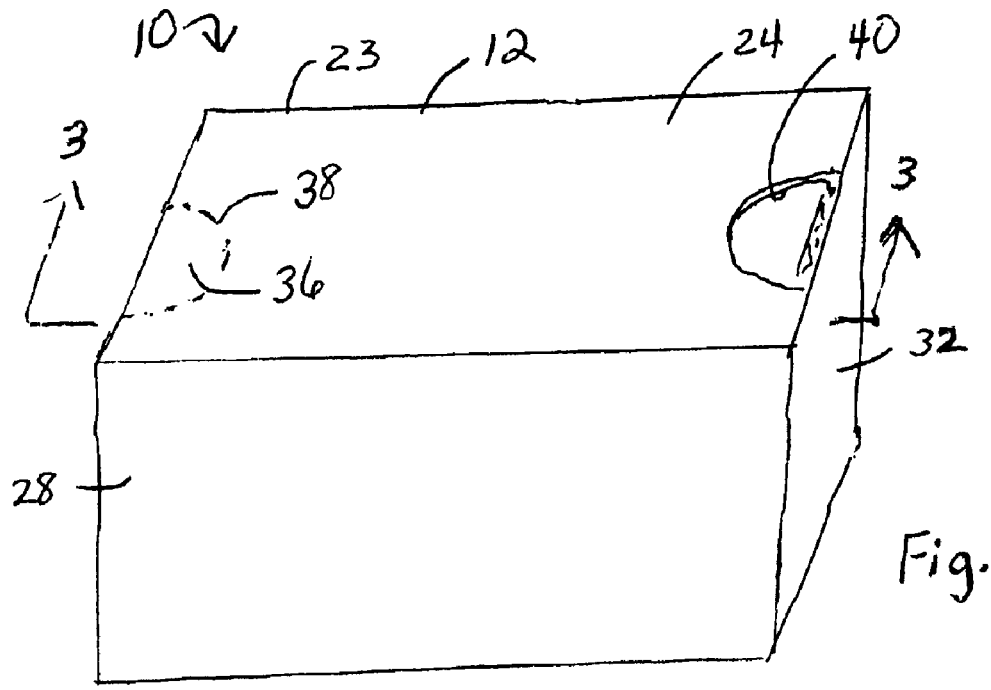
FIG. 1 is a perspective view of a top of a dispensing assembly of the present invention showing a dispenser for dispensing gloves having a removable portion defined by perforations on an upper wall such that, when removed, a dispensing opening is provided as shown on an opposite side of the upper wall.

Reference will now be made in detail to one or more embodiments of the invention, examples of which are illustrated in the drawings. Each example and embodiment is provided by way of explanation of the invention, and is not meant as a limitation of the invention. For example, features illustrated or described as part of one embodiment may be used with another embodiment to yield still a further embodiment. It is intended that the invention include these and other modifications and variations as coming within the scope and spirit of the invention.

Referring now to FIGS. 1-18 in general, and 1-4 in particular, the present invention provides a dispensing assembly 10. The dispensing assembly includes a dispenser 12 and a plurality of gloves 16 disposed therein.

Figure 2:
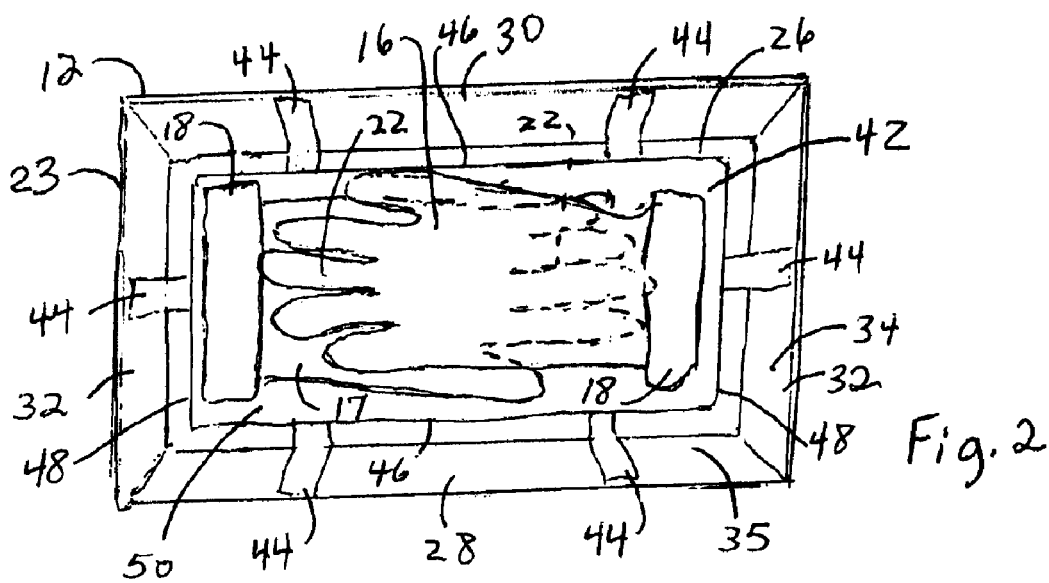
FIG. 2 is an upper plan view of the dispensing assembly of FIG. 1 but showing the upper wall removed, a pair of gloves disposed on a plate attached to the walls of the dispenser via a plurality of resilient bands, the gloves positioned in a finger-to-cuff arrangement such that cuffs are aligned on each end of the plate.

Turning now to the plurality of gloves 16, each glove 16 desirably, but not by way of limitation, includes a wrist area 17 which is positioned around a user's wrist, which may, by way of example, be turned back over an adjacent portion of the glove 16 to provide a cuff 18. The plurality of gloves 16 are desirably aligned into a stack 20 so that the wrist area 17 and cuff 18 (if present) of one glove 16 is positioned adjacent the finger and thumb areas 22 of the adjacent glove 16, however, the cuff 18 of every other glove 16 on each end of the stack 20 is desirably aligned together, as shown in FIG. 2.

Figure 4:
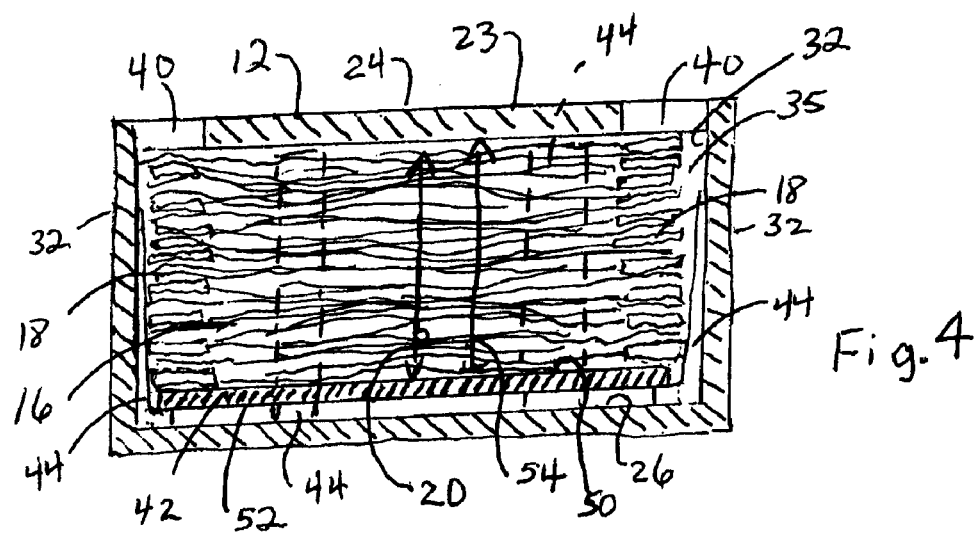
FIG. 4 is a sectional view similar to FIG. 3, but showing the position of the plate and resilient bands when fully loaded with gloves positioned on the plate.
Figure 5:
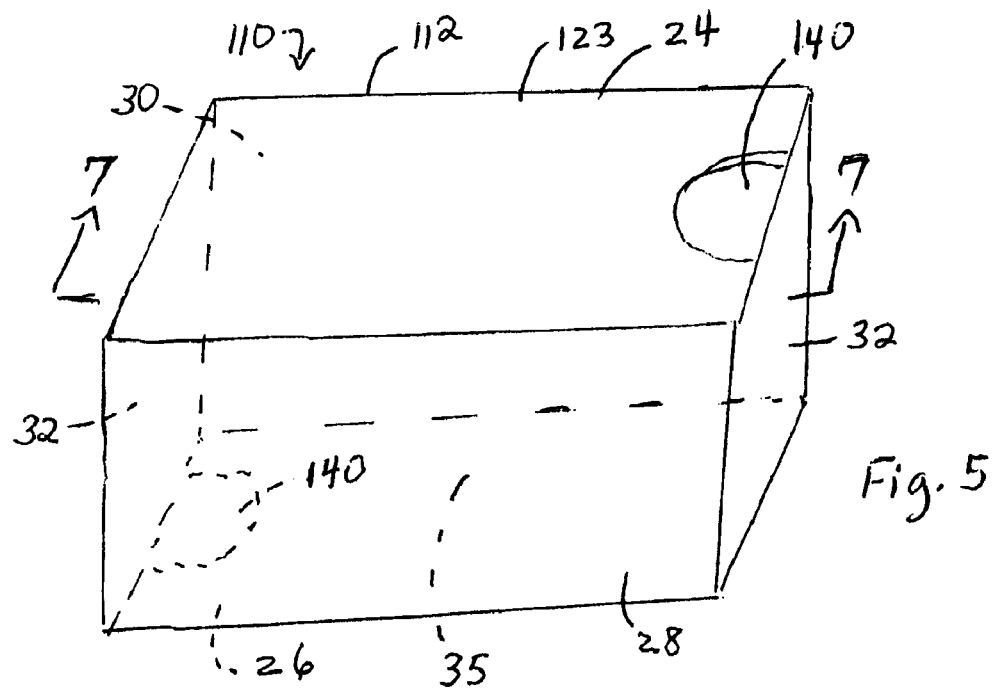
FIG. 5 is a perspective view of the top of another dispensing assembly of the present invention showing a dispenser for dispensing gloves having a dispensing opening on a lower wall of the dispenser (shown by phantom lines) and, on an opposite side of the dispenser, a dispensing opening in the upper wall.

Such an overlapping configuration is used to avoid asymmetry of the stack 20 of gloves 16. That is, the wrist area 17 of each glove 16 is often thicker and may have a rolled portion (not shown). If the wrist area 17 is folded back against itself to provide a cuff 18, the cuff 18 area of the glove 16 is twice as thick as the remaining glove 16. Due to the asymmetry in thickness, the plurality of gloves 16 aligned in a stack 20 by wrist area 17 or cuff 18 provide an asymmetrical stack due to this variation in thickness of each glove 16. This asymmetry results in unwanted and un-used space in the dispenser 12. When the gloves 16 are stacked in a cuff-to-finger/thumb alignment, this unwanted and unused space, as well as the asymmetry of the stack 20 is greatly reduced or eliminated, as shown in FIG. 4, yet cuffs 18 of gloves 16 are positioned next ot each other to permit easy withdrawal of one glove 16 at a time from the dispenser 12.

The dispenser 12 of the dispensing assembly desirably includes a housing 23 which further includes an upper wall 24 and a lower wall 26. The housing 23 also desirably includes a front wall 28, a back wall 30, and a pair of spaced-apart side walls 32. The front wall 28, back wall 30, and side walls 32 each cooperate with the upper wall 24 and lower wall 26 to form an inner surface 34 and space which defines an internal compartment 35 configured to hold the plurality of gloves 16. It will be appreciated that the configuration of the housing 23 is non-limiting, and the housing 23 may assume any configuration or combination of configurations.

The housing 23 of the dispenser 12 also desirably includes at least one, and desirably a pair of lines of weakness and/or perforated areas 36 which may be positioned on a wall, such as the upper wall 2, as shown in FIG. 1. When the lines of weakness and/or perforations 38 are separated and the perforated areas 36 are removed, a pair of dispensing openings 40 are provided in the housing 23 which permits the plurality of gloves 16 to be withdrawn from the housing 23 one at a time. The openings 40 may be provided in any wall or combination of walls.

The one or more dispensing openings 40 are desirably sized and configured to permit one-at-a-time dispensing of the plurality of gloves 16. Therefore, the one or more dispensing openings 40 are desirably positioned on the housing 23 to permit reasonably easy access to a user without causing excessive dispensing. Further, the openings 40 are sized and configured to limit contaminants into the internal compartment 35 of the housing 23, and to limit exposure of the gloves 16 therein to the glove(s) positioned directly against the dispensing openings 40. It will be understood that the dispensing openings 40 may assume any configuration(s).

The dispenser 12 includes additional features which provide versatility. While many dispensing assemblies are oriented as gravity-feed dispensing assemblies, the present dispensing assembly 10 includes a glove positioner including a plate 42 having a plurality of resilient bands 44 which eliminates the need for gravity-feed dispensing. The plate 42 has resilient bands 44 which permits the dispensing assembly 10 to be oriented to dispense at a horizontal, vertical, or oblique angle.

The plate 42 is desirably sized and configured to have slightly smaller dimensions relative to the dimensions of the lower wall 26. The plate 42 in the present embodiment for illustrative purposes only generally follows and may be slightly smaller than the dimensions of the inner surface 34 of the housing 23 and, in the present embodiment, is rectangular. It will be appreciated that this configuration of the plate 42 is intended as a non-limiting. The plate 42 therefore includes a pair of spaced-apart elongated sides 46 and a pair of comparatively shorter ends 48. The plate 42 also includes an upper surface 50 and a lower surface 52. The plate 42 is desirably, but not by way of limitation, coupled to the front and back walls 28, 30 and side walls 32 of the inner surface 34 of the housing 23 via the resilient bands 44.

The resilient bands 44 are desirably formed from a material which permits the bands to stretch and elongate under pressure but to return to their previous, much shorter length when the pressure is relieved. Such bands 44 may be formed from elastic, natural rubber, and other synthetic and/or natural materials, or combinations thereof, and so forth. The resilient bands may comprise springs made from metal, plastic, and so forth. Therefore, the bands 44 may comprise any mechanism and/or material, and so forth, so long as the resilient bands 44 operate as shown and/or described herein.

The resilient bands 44 may couple to the plate via any known manner, such as, by way of non-limiting example, heat sealing, stapling, adhering via adhesives, mechanically fastening, and so forth. The resilient bands 44 may extend a short distance under the plate 42 and couple thereto on the lower surface 52. Alternatively, the resilient bands 44 may extend completely under the plate 42 on the lower surface 52 to emerge on an opposite side 46 or end 48 of the plate 42 (not shown). In yet another alternative, some bands 44 may extend completely under the plate 42 and may not couple to the plate 42 and some bands may extend to just the lower surface 52 and couple to the plate 42 (not shown).

The bands 44 are oriented to pull the plate 42 toward the dispensing openings 40 as weight is relieved on the bands 44. The bands are not configured beneath the plate 42 to push the plate 42 toward one or more openings, because such an orientation of one or more bands would waste space within the internal compartment 35 of the housing 23, resulting in fewer gloves 16 which could be disposed in the internal compartment 35.

Figure 3:
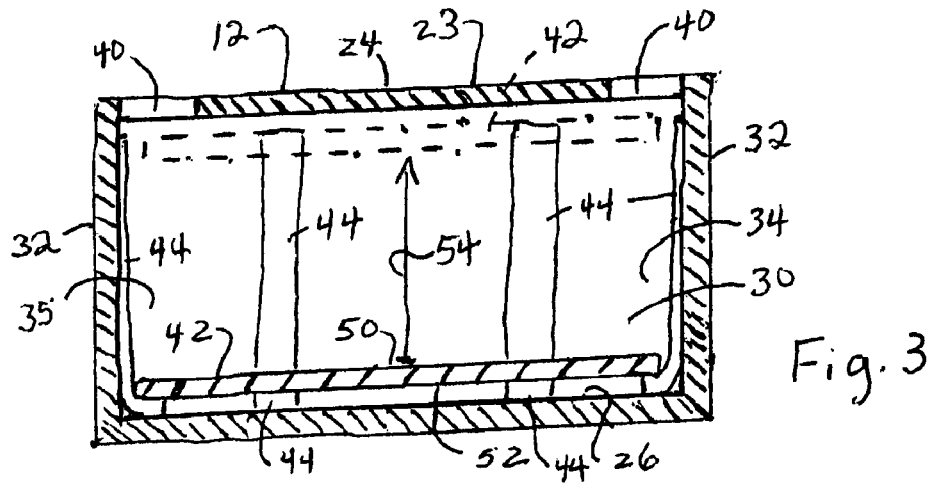
FIG. 3 is a sectional view of FIG. 1 taken along lines 3-3 showing the position of the plate and the resilient bands when the dispenser is fully loaded with gloves (not shown), and showing the position of the plate, represented by phantom lines, when the dispenser is empty.

In a method of withdrawing one or more gloves 16 form a dispenser assembly 10, a dispenser 12 having a housing 23 with at least one and desirably a pair of dispensing openings 40 is provided. The housing 23 is formed to include an inner surface 34 defining an internal compartment 35. The internal compartment 35 includes a plate 42 having resilient bands 44 which are attached to at least a portion of the inner surface 34 of the housing 23. The plate is configured to hold a plurality of gloves 16 desirably in a stack 20. The bands 44 are desirably formed to move the plate 42 within the housing 23 as a result of increased or decreased weight on the plate 42. The plurality of gloves 16 are arranged in the finger and thumb area 22 to cuff 18 orientation (FIG. 2) and are desirably arranged cuff-to-cuff in the generally symmetrical stack 20 and disposed on the plate 23 in the dispenser housing 23, as illustrated in FIG. 4. When the dispenser housing 23 is filled with the plurality of gloves 16 positioned in the stack 20, the weight of the stack 20 causes the bands 44 to fully extend so that the plate 42 is positioned next to or near the lower wall 26, as illustrated in FIGS. 3 and 4. As each glove 16 is removed from the dispenser housing 23, the weight on plate 42 decreases and the bands 44 begin moving the plate 42 in a direction 54 closer to the upper wall 24 of the housing 23. Desirably, the plate 23 moves to keep the gloves 16 closest to the openings 40 positioned against the openings 40. When nearly all of the gloves 6 have been withdrawn from the housing, the plate 42 is desirably positioned close to or against the upper wall 24 of the housing 23, as shown in FIG. 3 (via phantom lines). In this manner, as one or more gloves 16 are removed by users, the pressure of the bands 44 moves the plate 42 such that the glove positioned immediately beneath a glove which is removed is moved by the plate 42 to be positioned next to at least one dispensing opening(s) 40.

This action by the plate 42 and bands 44 limits contamination from entering the dispenser housing 23, because a user does not need to push his/her hand into the internal compartment 35 to obtain a glove 16. Further, the orientation of the stack 20 of gloves 16 on the plate 42 provides a generally symmetrical stack 20, which assists in removing unwanted space between the dispensing openings 44 and the gloves 16, further reducing contamination to the gloves 16 and the internal compartment 35 of the housing 23. Working in cooperation, the symmetry of the stack 20 along with the movement of the plate 42 via the bands 44 result in the control of the space within the internal compartment 35 and improved dispensing. The issues of unwanted space, which then may result when gloves fall out of the stack 20, which then results in unwanted clumping of gloves at the bottom of the dispenser housing 23, and all of the problems discussed earlier herein are greatly reduced or eliminated.

Figure 6:
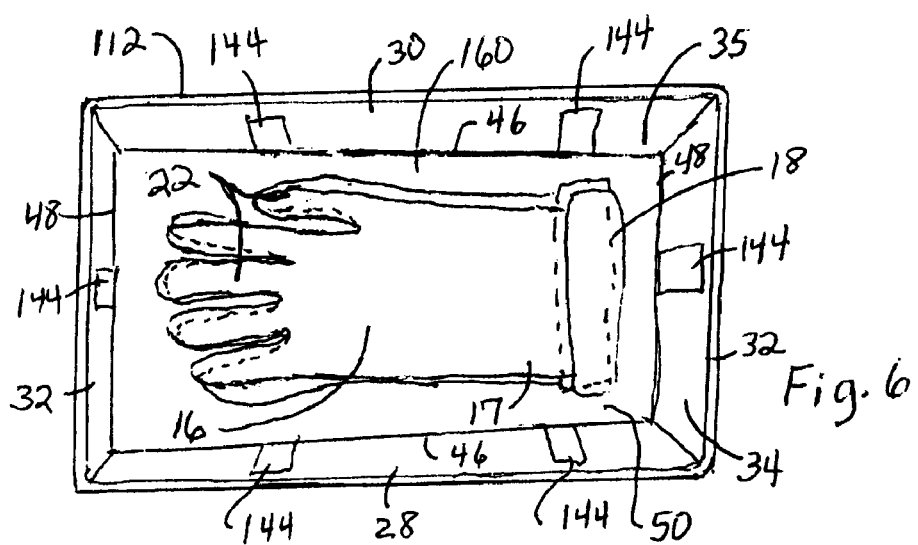
FIG. 6 is an upper plan view of the dispenser of FIG. 5 but showing the upper wall removed, a pair of gloves disposed on one plate attached to the walls of the dispenser via a plurality of resilient bands, the pair of glove positioned in a cuff-to-cuff arrangement.
Figure 7:
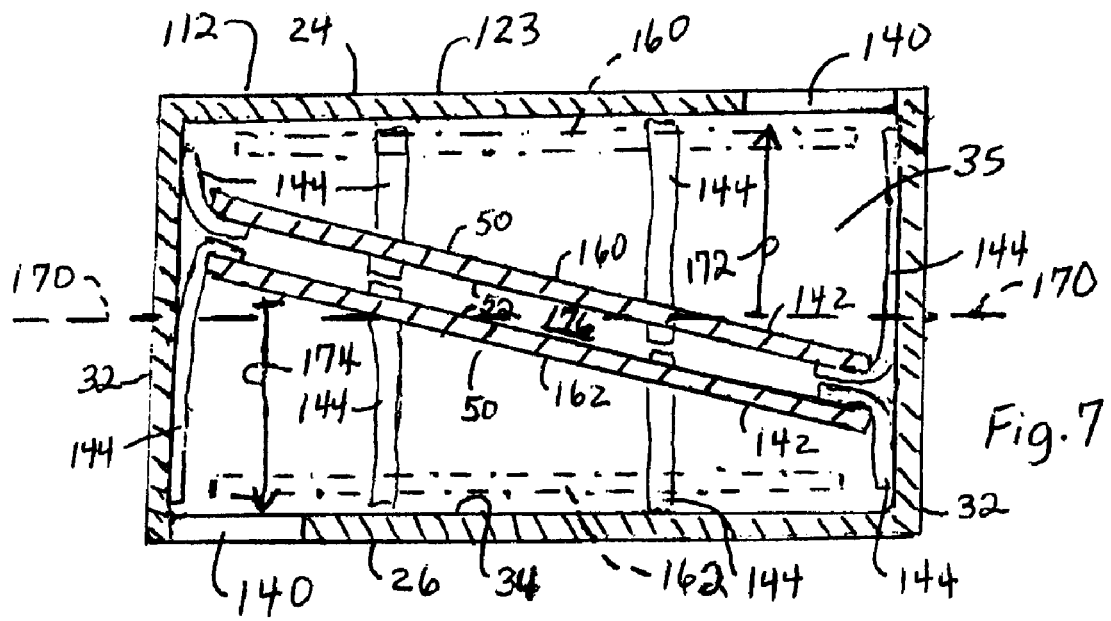
FIG. 7 is a sectional view of FIG. 5 taken along lines 7-7 showing the position of a first plate and its plurality of resilient bands when the first plate is fully loaded with gloves (not shown), and showing the position of the first plate (shown by phantom lines) when the gloves have been withdrawn, and also illustrating the position of a second plate and its plurality of resilient bands when the second plate is fully loaded with gloves (not shown) and showing the position of the second plate (illustrated by phantom lines) when the gloves have been removed therefrom.
Figure 8:
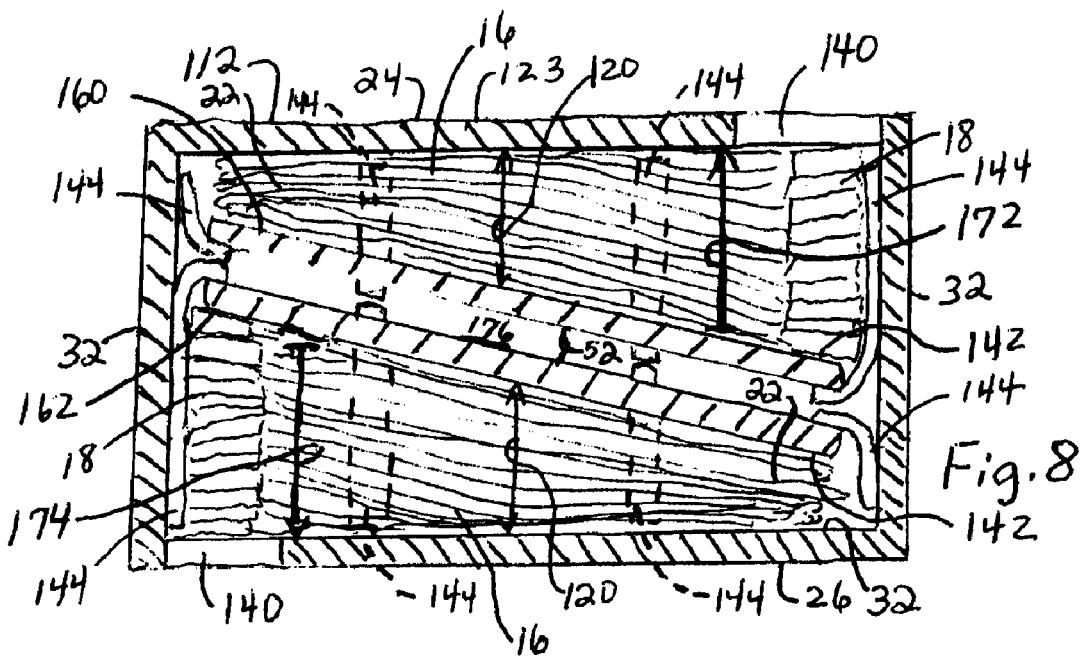
FIG. 8 is a sectional view similar to FIG. 7, but showing the position of the first plate and its resilient bands when fully loaded with gloves, and the position of the second plate and its resilient bands when fully loaded with gloves.
Figure 9:
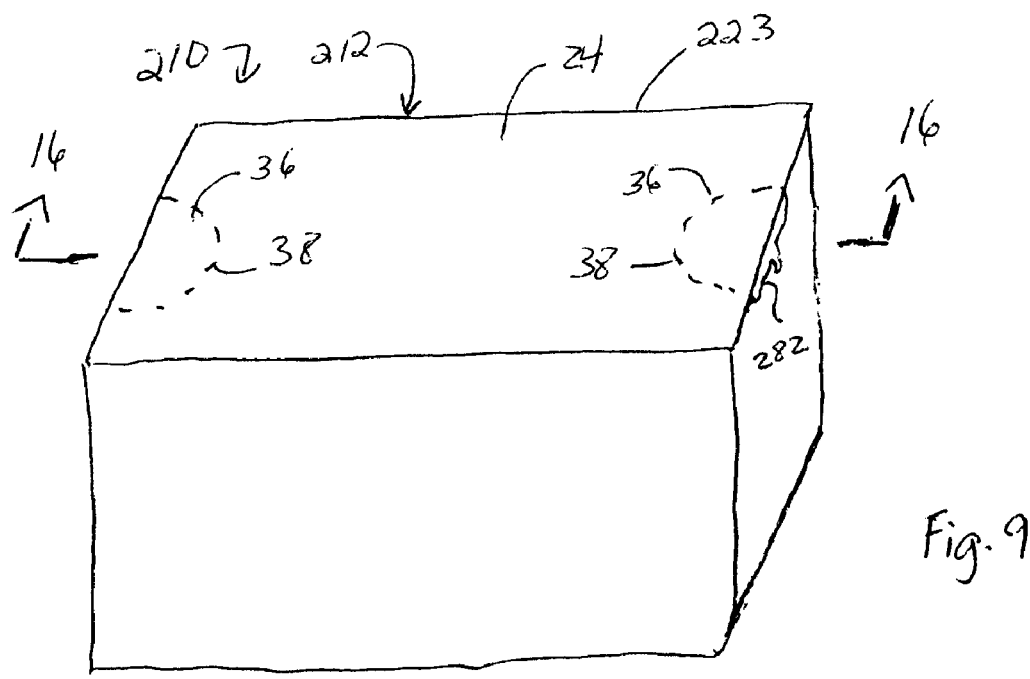
FIG. 9 is a perspective view of the top of another dispensing assembly of the present invention showing a dispenser for dispensing gloves having a pair of dispensing openings on an upper wall of the dispenser (shown by perforation lines) and an indented aperture provided in each side wall by each opening which is desirably covered by a clear or tinted seal (not shown) until removed for use, the indented aperture configured to assist a user in withdrawing one glove at a time from the dispensing opening.
Figure 10:
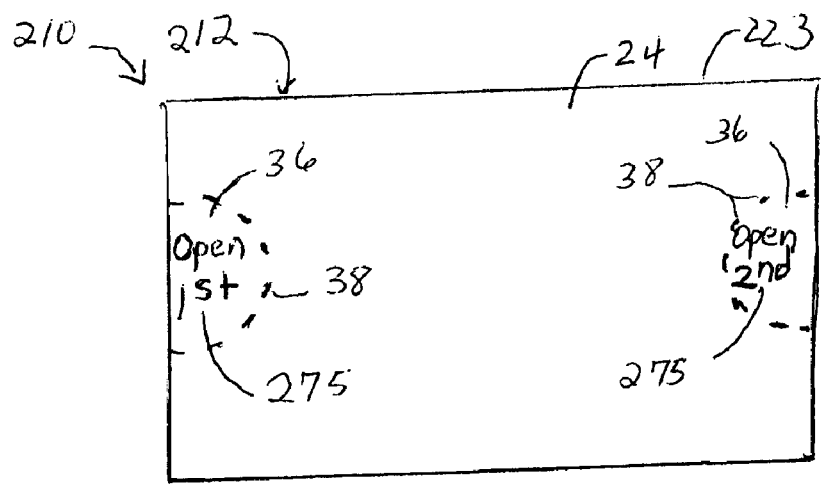
FIG. 10 is a top plan view of the dispenser of FIG. 9 but showing indicia associated with each dispensing opening which directs a user to open one opening first and another opening second to facilitate proper dispensing of gloves from the dispenser.
Figure 11:
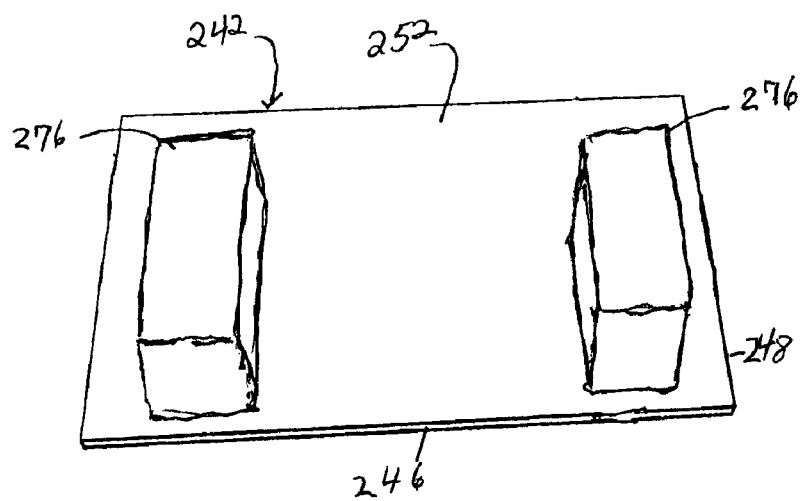
FIG. 11 is an upper perspective view of a plate used with the embodiments of FIGS. 9 and 10, showing the resilient material or blocks provided on one side thereof.
Figure 12:
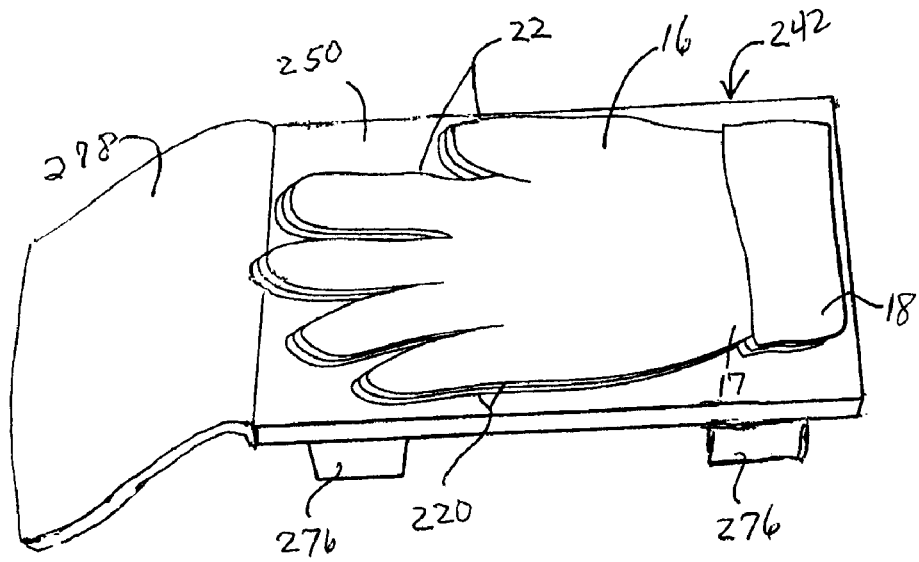
FIG. 12 is an upper perspective view of the plate of FIG. 11, but showing an opposite side of the plate with a stack of gloves disposed thereon and a flap attached to a portion of the plate.
Figure 13:
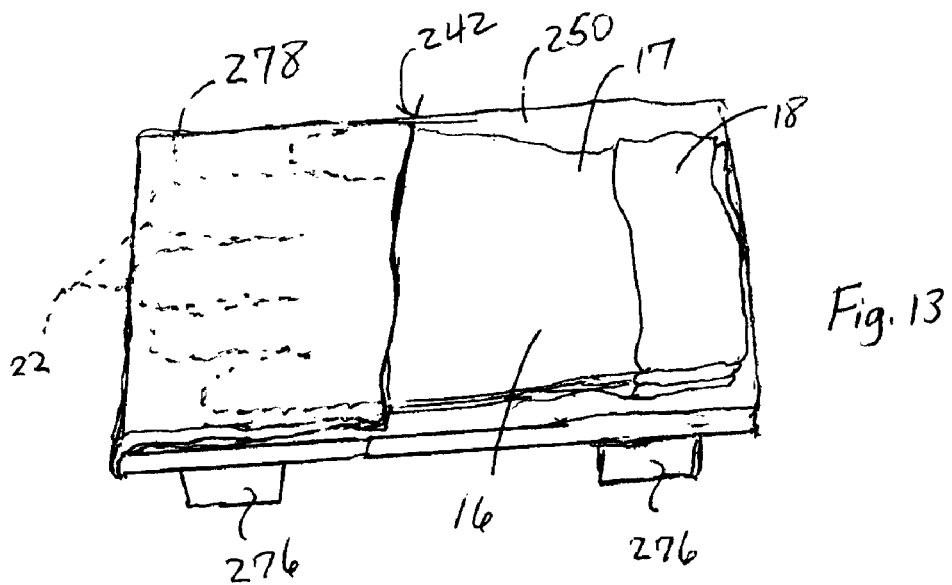
FIG. 13 is an upper perspective view of the plate of FIGS. 11 and 12, but showing the flap positioned over the finger/thumb areas (shown in phantom lines) of the stack of gloves.
Figure 14:
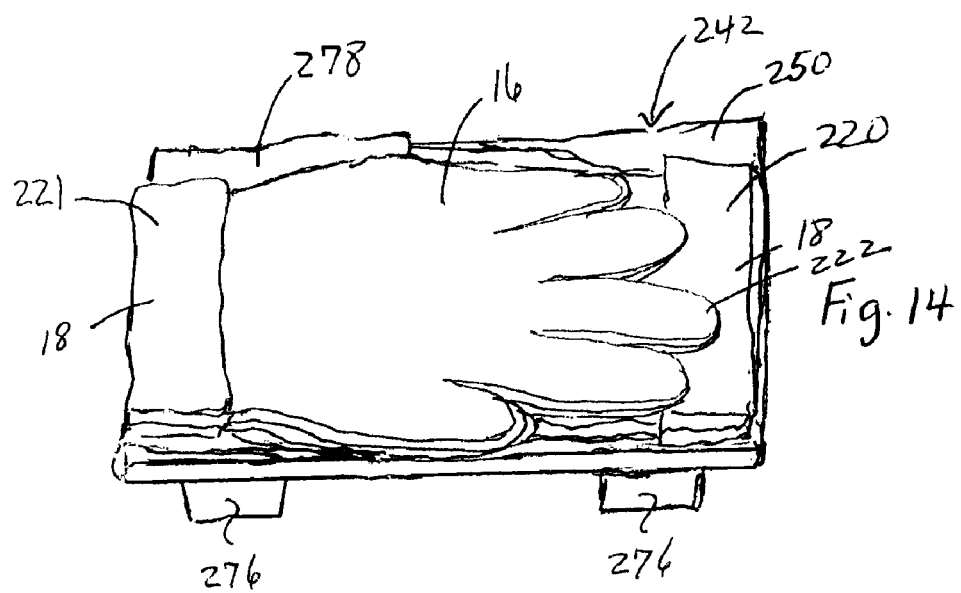
FIG. 14 is an upper perspective view of the plate of FIGS. 11-13, but showing another, second stack of gloves positioned on the plate such that the cuffs of the second stack are positioned on the flap which is positioned over the finger/thumb areas of the first stack.
Figure 15:
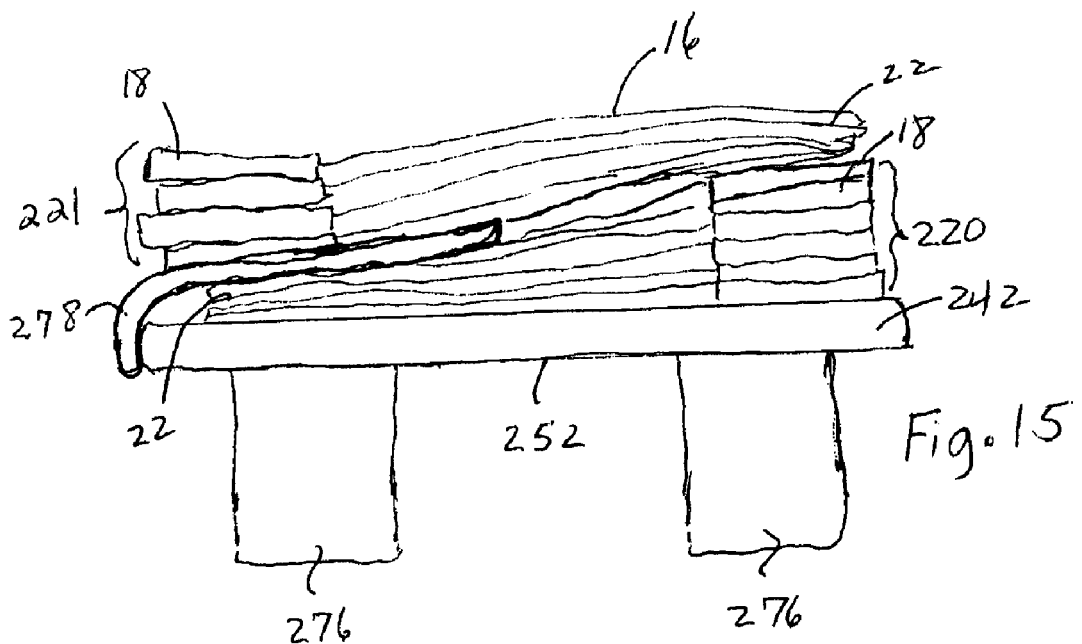
FIG. 15 is a side view of FIG. 14; showing the plate with two stacks of gloves divided partially by the flap.
Figure 16:
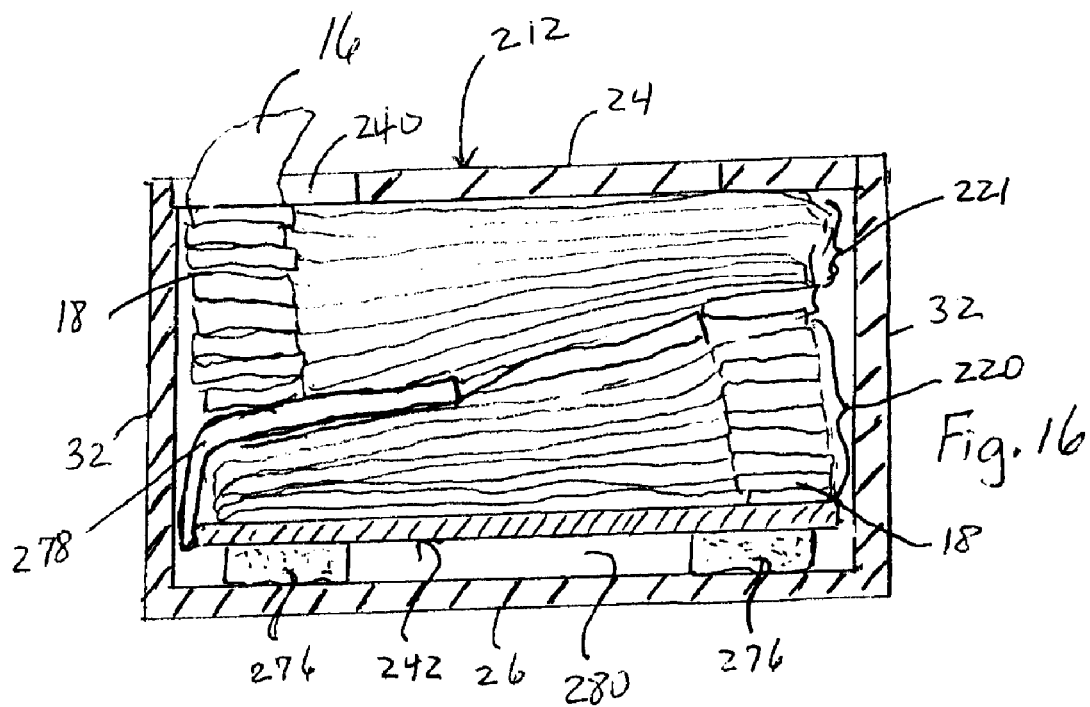
FIG. 16 is a sectional view of FIG. 9 taken along lines 16-16, showing the plate and stack of gloves of FIGS. 14 and 15 positioned in the dispenser for dispensing, gloves from the second stack being withdrawn from the dispenser first.

In another embodiment of the invention, the dispensing assembly 110 shown in FIGS. 5-8 is substantially similar to the dispensing assembly 10 shown in FIGS. 1-4 and described in detail herein, except that the dispenser 112 includes a housing 123 which includes a pair of plates 142 (each of which includes all of the characteristics previously shown and described in detail for a plate 42), each having resilient bands 144 coupled thereto, as illustrated in FIGS. 7 and 8. In addition, each of the pair of plates 142 holds a stack 120 of gloves 16 which are provided stacked in a cuff-to-cuff orientation, as shown in FIGS. 6 and 8. The dispenser housing 123 may include a pair of lines of weakness or perforated areas (not shown) having perforations (not shown) which, when the perforated areas are removed, result in a pair of dispensing openings 140, which may be positioned on walls opposite one another.

This orientation is created because users frequently wish to withdraw a glove 16 by its wrist area 17 or cuff 18, and do not wish to touch the hand or finger and thumb area 22 of the glove 16 to withdraw or remove it from a dispenser. This desire by users requires that the plurality of gloves 16 be stacked with wrist areas 17 next to each other or, when a cuff 18 is present, cuff-to-cuff.

The cause of an asymmetry in the stack 120 which occurs due to this orientation has been discussed above, as have some of the problems associated therewith. Due to this asymmetry, unwanted space is provided or occurs as gloves 16 are withdrawn from the stack 120 resulting in one or more gloves 16 within the stack 120 falling out of alignment, therefore interfering with the desirable one at a time dispensing of each of the plurality of gloves 16 from the housing 123. The resulting space which occurs when gloves 16 fall out of alignment may cause a user to reach into the dispenser housing 123 via the dispensing opening 140, resulting in further contamination of gloves 16 and the internal compartment 35 of the housing 123. This action results in more unaligned gloves 16, more opportunity for contamination to enter the dispensing opening(s) 140 and contaminate gloves 16 in the internal compartment 35, and it will be appreciated that the problems associated with cuff-to-cuff dispensing continue to compound.

The problems of unwanted space in the housing 123 caused by a stack 120 of gloves 16 which form cross-section which may be generally trapezoidal may be greatly reduced or eliminated when two stacks 120 of gloves 16 are provided, one stack 120 positioned on each of a pair of plates 142. Desirably, the pair of plates 142 are coupled via each plate's 142 plurality of resilient bands 144 to dispense, desirably, opposite each other in the housing 123.

The dispenser housing 123 desirably, but not by way of limitation, includes a dispenser opening 140 in an upper wall 24 and a dispenser opening 140 in a lower wall 26 as well. A first plate 160 of the pair of plates 142 is desirably positioned such that its plurality of bands 142 are positioned desirably on the inner surface 34 of the front and back walls 28, 30 and the side walls 32 such that, in an extended position when fully loaded with a stack 120 of gloves 16 in a cross-section, the first plate 160, the side walls 32 and the upper wall 24 form a generally trapezoidal shape or configuration, as shown in FIGS. 7 and 8.

Similarly, a second plate 162 of the pair of plates 142 is desirably positioned such that its plurality of bands 142 are positioned desirably on the inner surface 34 of the front and back walls 28, 30 and the side walls 32 such that, in an extended position when fully loaded with a stack 120 of gloves 16 in a cross-section, the second plate 162, the side walls 32 and the lower wall 26 form a generally trapezoidal shape or configuration, as shown in FIGS. 7 and 8.

When the dispenser housing 123 is filled with a full stack 120 of gloves 16 on each of the first and second plates 160, 162, the weight of each stack 120 causes the bands 144 on each of the first and second plates 160, 162 to fully extend so that the first and second plates 160, 162 are positioned such that the cuffs 18 of each stack 120 extends below a midline 170 (positioned about midway through the sidewalls) of the dispenser housing 123 and each finger area 22 of each stack 120 extends above the midline 170, as illustrated best in FIG. 8. As each glove 16 is removed from the dispensing openings 140, the weight on each first and second plate 160, 162 decreases and the bands 144 begin moving the first and second plates 160, 162 in opposite directions 172, 174, respectively. This action results in the first plate 160 moving closer to the upper wall 24 of the housing 123 and the second plate 162 moving closer to the lower wall 26. Desirably, each of the first and second plates 160, 162 moves to keep the gloves 16 closest to the openings 140 positioned against the openings 140. When nearly all of the gloves 16 have been withdrawn from the housing 123, the first and second plates 160, 162 are desirably positioned close to or against the upper wall 24 and lower wall 26, respectively, of the housing 23, as shown in FIG. 7 (via phantom lines). In this manner, as one or more gloves 16 are removed by users, the pressure of the bands 144 moves the first and second plates 160, 162 such that the glove positioned immediately beneath a glove which is removed is moved by the plate 42 to be positioned next to or against the adjacent dispensing opening 140.

It will be understood that the dispenser 112 may be moved such that the side walls 32 of its housing 123 become the upper and lower walls. Similarly, the previous upper and lower walls 24, 26 become the new side walls. Further, the dispenser housing 123 may be rotated such that the upper wall 24 becomes the lower wall, while the lower wall 26 becomes the new upper wall, and so forth. It will be appreciated that the present embodiment facilitates horizontal dispensing, vertical dispensing, or dispensing at an oblique angle.

It will be appreciated, as illustrated best in FIGS. 7 and 8, that the problems previously caused due to an asymmetry of a stack 120 of gloves 16 stacked cuff-to-cuff is solved by using the trapezoidal or, alternatively, triangular cross-section of the stacks 120 of gloves 120 to fill a square or rectangular dispenser housing 123, thereby removing or controlling unwanted space which results from the asymmetry and from dispensing and depleting the gloves 16 from the dispenser 112. Utilizing a pair of plates 142 with resilient bands to create a space 176 as the gloves 16 are dispensed from each dispensing opening 140 and from each plate 142, greatly reduces or eliminates the previous problems of gloves which became unaligned and fell from the stack and clumped together in the bottom of the dispenser. The pair of plates 142 act as the single plate 42 previously shown and described herein acts, to hold the gloves 16 next to the dispensing openings 140 so that a user is not required to place a portion of his/her hand into the dispenser 112 to obtain a glove. The pair of plates 142 also assists in preventing contaminants from falling into one or more dispensing openings 140 when, after dispensing an amount of gloves 16, a space is formed had previously been formed between the dispensing opening and the remaining gloves (not shown).

In yet another embodiment of the invention, the dispensing assembly 210 shown in FIGS. 9-18 is substantially similar to the dispensing assembly 10 and 110 shown in FIGS. 1-8 and described in detail herein, except that the dispenser 212 includes a housing 223 which includes a glove positioner including a plate 242 (each of which includes all of the characteristics previously shown and described in detail for a plate 42) which includes at least one resilient material or block, and in this embodiment, but not by way of limitation, a pair of resilient blocks, positioned on a lower surface 252 thereof, as illustrated in FIGS. 11-18. The dispenser housing 223 may include a pair of lines of weakness and/or perforated areas 236 having perforations 238 which, when the perforations 238 are separated and the perforated areas 236 are removed, result in a pair of dispensing openings 240 formed in one or more wall(s). Indicia 275 may be provided adjacent and/or on each perforated area 236 to direct a user as to which of the two dispensing openings 240 to open first.

In this embodiment, the plate 242 is desirably pushed toward the dispensing opening(s) 240 via the resilient material. Such resilient material or blocks 276 may be made from a natural or synthetic foam rubber or sponge. Other resilient material(s) such as, but not by way of limitation, rubber, rubber bands, elastic bands, O-rings, and so forth, may be used to push or pull the plate 242 toward the opening(s) 240.

A first stack 220 of gloves 16 is positioned on an upper surface 252 of the plate 242. The first stack 220 is oriented so that the gloves 16 are stacked cuff-to-cuff (or wrist-to-wrist), as is often preferred by users, as described herein. As discussed previously, this method of stacking results in asymmetry in the stack 220. A flap 278 is overlapped over the finger/thumb areas 22 of the first stack 220 of gloves 16. A second stack 221 of gloves 16 which are stacked cuff-to-cuff is positioned on the plate 242, with the cuffs 18 of the second stack 221 overlapping the flap 278. This orientation, with the cuffs 18 of each of the first and second stacks 220, 221 of gloves 16 positioned at opposite ends 48 of the plate 242 results in a balancing of the asymmetry created by each stack 220, 221 individually, as illustrated generally in FIGS. 15 and 16, such that the plate 242 is generally parallel to the dispensing wall(s) or surface(s), in the present embodiment, the upper wall 24.

The flap 278 is desirably, but not by way of limitation, coupled to the housing or the plate 242. The flap 278 may be formed from any material(s) which permit the flap 278 to operate as shown and/or described herein.

Figure 17:
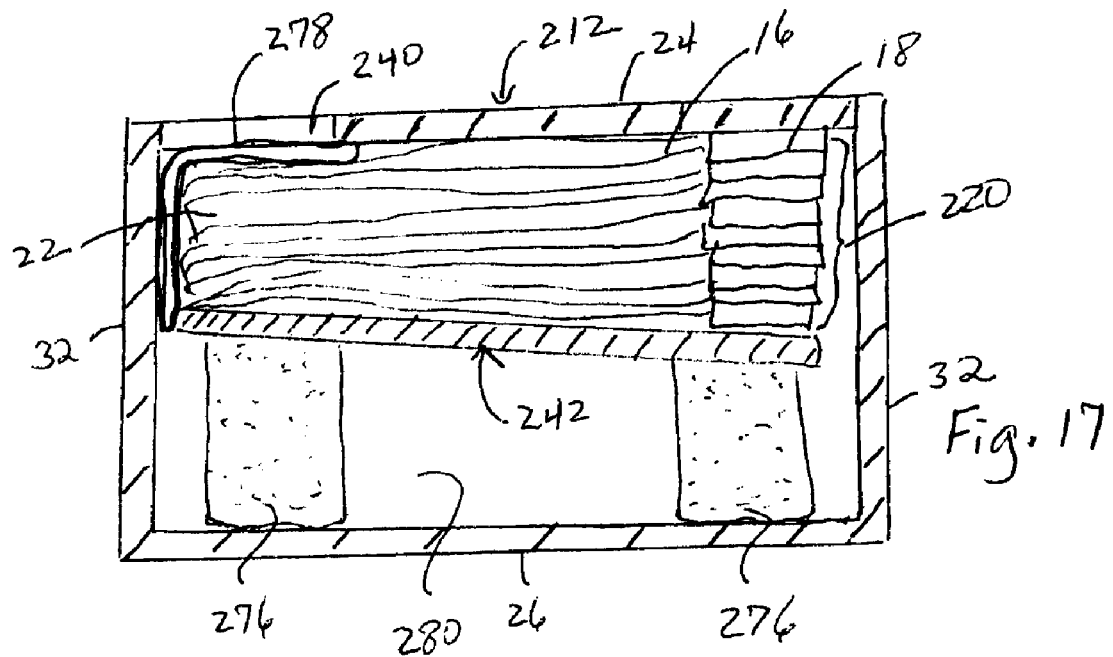
FIG. 17 is a sectional view similar to FIG. 16, but showing the flap blocking the first opening after the gloves in the second stack are removed so that the perforated area and perforations of the second opening will be opened by a user.
Figure 18:
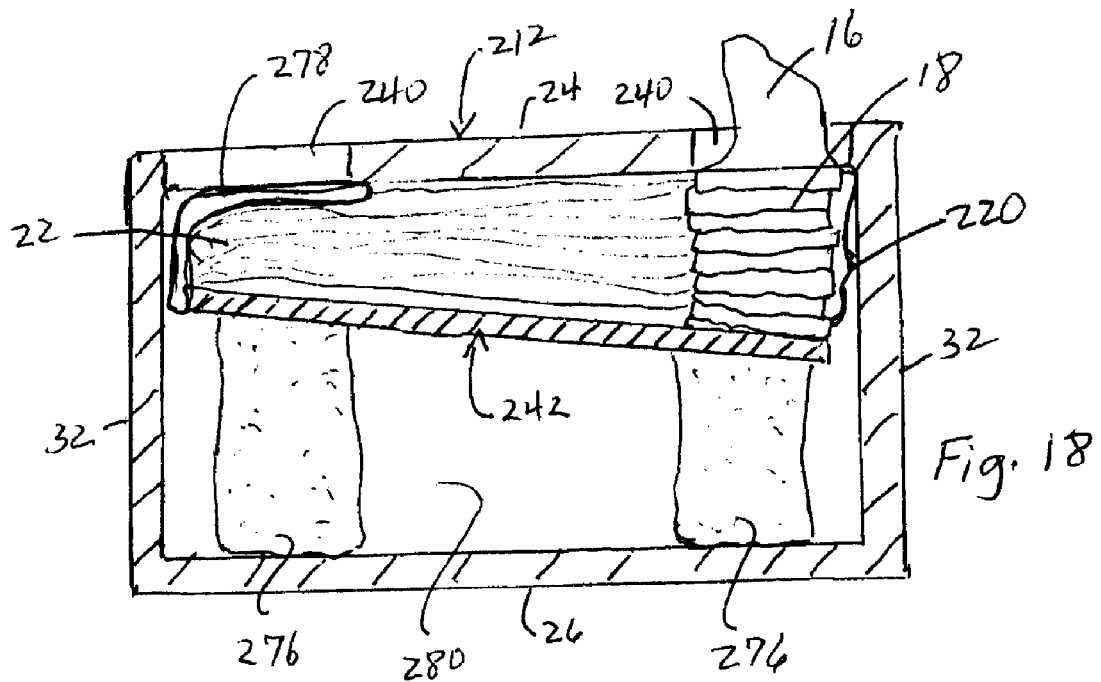
FIG. 18 is a sectional view similar to FIG. 17, but showing the second opening opened so that the gloves in the first stack may be withdrawn from the dispenser.

However, as the resilient material 276 urges and pushes the plate 242 toward and against one or more dispensing openings 240, and the gloves 16 of the second stack 221 are withdrawn from the dispenser 212, the asymmetry reoccurs again, as shown in FIGS. 17 and 18, resulting in a trapezoidal cross-section. The resilient material 276 and the plate 242 (collectively the glove positioner) bias the asymmetrical stack 220 toward the dispenser opening(s) 240.

The flap 278 prevents users from withdrawing gloves 16 from the first stack 220 via the finger/thumb areas 22. Withdrawing the gloves 16 from the first stack 220 via the finger/thumb areas 22 is likely to result in gloves 16 in the stack 220 being pulled out of alignment, gloves bunching in the dispenser, and gloves falling down into the dispenser housing 123, resulting in contamination of gloves 16. The flap 278 and/or the perforated areas 236 desirably will have indicia 275 that directs a user to open another of the pair of dispensing openings 240 to expose a cuff positioned thereagainst of the first stack 220 of gloves 16. While the glove positioner biases the first stack 220 against the dispensing opening(s) 240 in a direction 282 toward the dispensing opening(s) 240, the asymmetry of the stack 220 of gloves 16 is controlled such that the gloves are held and maintained in a dispensing alignment adjacent the dispensing opening even though the stack 220 forms a trapezoidal cross section within the dispenser 212. Therefore, it will be appreciated that the problems associated with cuff-to-cuff dispensing are overcome to permit one-at-a-time dispensing of gloves without frustration or waste. Further, the problems of space 280 within the housing 223 is controlled.

An indented aperture 282 may be provided adjacent the perforated area(s) 236. The indented aperture 282 is desirably formed by perforations (not shown) which are separated, or is provided as an aperture with a removable seal (not shown). This indented aperture 282 assists a user in removing one glove at a time from the dispenser 212.

The dispenser 12, 112, 212 and the plate(s) 42, 142, 242 may be constructed from any material or combination of materials which permit it to operate as shown and/or described herein. Such materials may include, for example, but not by way of limitation, cardboard, paperboard, plastic, metal, polymer film, and so forth.

While the present invention has been described in connection with certain preferred embodiments, it is to be understood that the subject matter encompassed by way of the present invention is not to be limited to those specific embodiments. On the contrary, it will be appreciated that some elements and/or articles may be used with other elements or articles. It is intended for the subject matter of the invention to include all alternatives, modifications and equivalents as can be included within the spirit and scope of the invention.

What is claimed is:

1. A dispensing assembly adapted for dispensing gloves, the dispensing assembly comprising:
a dispenser having a housing comprising a plurality of walls which cooperate to form an inner surface and an internal compartment, the dispenser configured to hold a stack of gloves and a stack of gloves disposed in the dispenser, the dispenser including a dispensing opening, the stack of gloves positioned on a glove positioner including a resilient material such that the stack of gloves forms a trapezoidal cross-section within the internal compartment of the dispenser, the glove positioner biasing the stack of gloves toward the dispensing opening and a portion of the housing such that the glove positioner controls the stack of gloves and space in the internal compartment of the dispenser to prevent gloves from moving out of the stack and into the space, the stack of gloves biased against the dispensing opening to permit easy and reliable withdrawal of each glove therefrom, and a flap positioned over at least a portion of the stack of gloves, whereby the flap encourages a user to withdraw a glove via a cuff of the glove and prevents withdrawal of a glove via a finger/thumb area.

2. The dispensing assembly of claim 1, wherein the glove positioner includes a plate.

3. The dispensing assembly of claim 2, wherein the plate is biased toward the dispensing opening.

4. The dispensing assembly of claim 3, wherein the plate is biased toward the dispensing opening via a resilient material.

5. The dispensing assembly of claim 1, wherein the dispenser is rectangular and the stack of gloves defines a trapezoidal cross-section within the internal compartment and the glove positioner biases the stack of gloves against a portion of the housing such that the stack of gloves continues to form a trapezoidal cross-section until all of the gloves of the stack are withdrawn from the dispenser.

6. A dispensing assembly adapted for dispensing gloves, the dispensing assembly comprising:
a dispenser having a housing comprising a plurality of walls which cooperate to form an inner surface and an internal compartment, the dispenser configured to hold a stack of gloves and a stack of gloves disposed in the dispenser, the dispenser including a pair of spaced-apart dispensing openings, the stack of gloves positioned on a glove positioner having a pair of opposing ends such that gloves are arranged in an alternating cuff-to-finger/thumb alignment so that the cuffs are adjacent one of the dispensing openings, the glove positioner including a resilient material which biases the stack of gloves toward the dispensing opening and a portion of the housing such that the glove positioner controls the stack of gloves and space in the internal compartment of the dispenser to prevent gloves from moving out of the stack and into the space, the stack of gloves biased against the dispensing openings to permit easy and reliable withdrawal of each glove therefrom.

7. The dispensing assembly of claim 6, wherein the glove positioner includes a plate.

8. The dispensing assembly of claim 7, wherein the plate is biased toward the dispensing opening via bands which are coupled to the plate.

9. The dispensing assembly of claim 6, wherein the dispenser is rectangular and the stack of gloves defines a rectangular cross-section within the internal compartment and the glove positioner biases the stack of gloves against a portion of the housing such that the stack of gloves continues to form a rectangular cross-section thereby controlling the glove alignment and the space within the dispenser until all of the gloves of the stack are withdrawn from the dispenser.

10. A dispensing assembly adapted for dispensing gloves, the dispensing assembly comprising:
a dispenser having a housing comprising a plurality of walls which cooperate to form an inner surface and an internal compartment, the dispenser configured to hold a first and second stack of gloves disposed in the dispenser, the dispenser including a pair of dispensing openings, the first and second stack of gloves each respectively positioned on a first and second glove positioner that are closely adjacent to each other, each first and second glove positioner including a resilient material that moves all of each glove positioner toward one of the dispensing openings, each first and second stack of gloves forming a trapezoidal cross-section within the internal compartment of the dispenser, each glove positioner biasing its respective first and second stack of gloves toward at least one of the pair of dispensing openings and at least one portion of the housing such that each of the pair of glove positioners controls its respective first and second stack of gloves and space in the internal compartment of the dispenser to prevent gloves from moving out of their respective stacks and into the space, the first and second stack of gloves each positioned to permit easy and reliable withdrawal of each glove from each first and second stack, and a flap positioned over at least a portion of each stack of gloves, whereby the flap encourages a user to withdraw a glove via a cuff of the glove and prevents withdrawal of a glove via a finger/thumb area.

* * * * *